United States Patent
Glattstein

(10) Patent No.: US 7,374,946 B2
(45) Date of Patent: May 20, 2008

(54) METHOD FOR THE DETECTION OF COMPOUNDS COMPRISING METHYLENEDIOXYPHENYL

(75) Inventor: Baruch Glattstein, Jerusalem (IL)

(73) Assignee: Baruch Glattstein, Jerusalem (IL)

( * ) Notice: Subject to any disclaimer, the term of this patent is extended or adjusted under 35 U.S.C. 154(b) by 0 days.

(21) Appl. No.: 10/499,719

(22) PCT Filed: Dec. 19, 2002

(86) PCT No.: PCT/IL02/01024

§ 371 (c)(1),
(2), (4) Date: Jun. 21, 2004

(87) PCT Pub. No.: WO03/052426

PCT Pub. Date: Jun. 26, 2003

(65) Prior Publication Data

US 2005/0130312 A1 Jun. 16, 2005

(30) Foreign Application Priority Data

Dec. 19, 2001 (IL) ........................ 147185

(51) Int. Cl.
*G01N 33/00* (2006.01)
*G01N 33/53* (2006.01)
*G01N 21/75* (2006.01)

(52) U.S. Cl. .................... 436/106; 436/816; 436/901; 436/166

(58) Field of Classification Search ............... 436/106, 436/816
See application file for complete search history.

(56) References Cited

FOREIGN PATENT DOCUMENTS

| DE | WO 00/36423 | * | 6/2000 |
|---|---|---|---|
| WO | WO 98/45714 A1 | | 10/1998 |
| WO | WO 00/36423 A1 | | 6/2000 |

OTHER PUBLICATIONS

H. Yamada, S. Ikeda-Wada, K. Oguri, Highly Specific and Convenient Color Reaction for Methylenedioxymethamphetamine and Related Drugs Using Chromotropic Acid. Application as a Drug Screening Test, Journal of Health Science, 45(6)303-308(1999).*

C.L. O'Neal, D.J. Crouch, A.A. Fatah, Validation of twelve chemical spot tests for the detection of drugs of abuse, Forensic Science International 109 (2000) 189-201.*

Murray S. Blum, Insecticide Synergists: Colorimetric Determination of Small Quantities of Methylenedioxyphenyl-Containing Pyrethrum Synergists, Feb. 1955, ACS Journal of Agricultural and Food Chemistry, vol. 3 No. 2, pp. 122-124.*

Choi, Myung, et al, "A simple device of the dry tetrabromophenolphthalein ehtyl ester reagent strip for the detection of metamphetamine", Arch. Pharm. Res. (1993). 16(3):227-230.

DeMayo, M.M., et al, "Colorimetric determination of 3,4-methylenedioxyamphetamine (MDA)", Journal—Forensic Science Society . (1972). 17(2):444-446.

Dingjan, H.A., et al "Colour tests for the identification of alkaloids (and related compounds): A literature review and a study of colour changes in relation to time", Pharmaceutisch Weekblab. (Apr. 4, 1980). Amsterdam, NL.115(14):445-467.

Yamada, Hideyuki, et al, "Highly specific and convenient color reaction for methylenedioxymethamphetamine and related drugs using chromotropic acid. Application as a drug screening test", Journal of Health Science. (1999). 45(6):303-308.

Clarke, E.G.C., "Isolation and Identification of Drugs", Pharmaceutical Press (1986), pp. 663-669.

Feigel, F., "Spot Tests in Organic Analysis", (1966), p. 137-140.

Beroza, M., "Identification of 3,4-Methylenedioxyphenyl Synergists by Thin-Layer Chromatography", Agriculture and Food Chemistry (1963), pp. 51, vol. 11, No. 1.

Jungreis, E., Spot Test Analysis, Clinical Environmental, Forensic and Geochemical Applications, (1984), table of contents only.

* cited by examiner

*Primary Examiner*—Lyle A. Alexander
*Assistant Examiner*—Keri A Moss
(74) *Attorney, Agent, or Firm*—Browdy & Neimark

(57) ABSTRACT

Process and a test kit for the detection of drugs of methylenedioxy amphetamine family and derivatives, are disclosed. The process comprises (a) sampling sufficient amount of a material, suspected to be examined comprise of said methylenedioxyphenyl group; (b) admixing said sample with a sufficient amount of a strong acid reagent; and (c) detecting color gradual appearance and determining accordingly the presence of said methylenedioxy amphetamine drugs in predetermined interval of time. The test kit comprises a strong acid reagent; a color vs time chart comprising means for the detection of a specific drug by means of color and time of appearance, a reaction chamber wherein suspected material and said strong acid reagent are admixed and color is indicated; a sampler having means to collect sufficient amount of suspected material to be tested and to insert it to the reaction chamber.

16 Claims, No Drawings

METHOD FOR THE DETECTION OF COMPOUNDS COMPRISING METHYLENEDIOXYPHENYL

FIELD OF THE INVENTION

The present invention relates to a method for the detection of compounds comprising interalia methylenedioxyphenyl groups. Furthermore, the present invention relates to a testing kit for the detection of drugs, including drugs of the ecstasy family. More specially, the present invention relates to a process and to a testing kit for a reliable detection of drugs comprising interalia methylenedioxyphenyl groups, wherein said compounds are selected from N-methyl-3,4-methylenedioxymethamphetamine (MDMA, 'ECSTASY'); 3,4-methylenedioxyamphetamine (MDA), 3,4-methylenedioxyethylamphetamine (MDEA); 3-methoxy-4,5-methylenedioxyamphetamine (MMDA); N-methyl-1-(3,4-methylenedioxyphenyl)-2-butaneamine (MBDB); or 3,4-methylenedioxyphenyl-2-(N-ethyl)butaneamine (MD-2-EB).

BACKGROUND OF THE INVENTION

On numerous occasions police officers need to determine rapidly whether or not suspected materials contain drugs and thus quickly establish probable cause. A rapid and facile test kit can help to detect the presence of the drug or alternatively to determine whether a tested sample definitely is a drug.

The quickest process known today for drug detection is a color test in which the response of the drug to a specific reagent makes it possible to assign the drug to one or more classes.

Chemical spot test kits have been commercially developed in order to obtain sufficient evidence to detain a drug peddler or drug user. Those kits are used today for the detection of narcotics and drugs of abuse by many law enforcement agencies.

The commercial test kits for the identification of drugs containing methylenedioxyphenyl group such as N-methyl-3,4-methylenedioxymethamphetamine (i.e., MDMA or 'ECSTASY'); 3,4-methylenedioxyamphetamine (i.e., MDA), 3,4-methylenedioxyethylamphetamine (i.e., MDEA); 3-methoxy-4,5-methylenedioxyamphetamine (i.e., MMDA); N-methyl-1-(3,4-methylenedioxyphenyl)-2-butaneamine (i.e., MBDB); or 3,4-methylenedioxyphenyl-2-(N-ethyl)butaneamine (i.e., MD-2-EB) are based on the famous Marquis sulfuric acid—formaldehyde reagent which gives a purple/black or blue/black color (ODV, Inc, NIK, Armour Holding Inc.). This kit, based on sulfuric acid-formaldehyde, is sold also through the Internet for the detection of "Ecstasy", becoming a serious problem in Europe and North America. The kits are sold by Green Party Drugs Group in the UK (E-Z Test™) and by US based Dancesafe organization (http://www.ecstasy.org).

Clark ("Isolation and Identification of Drugs" Pharmaceutical Press, 1986) lists tens of drugs that respond in the same way or similar way to Marquis reagent to MDMA type compound. Furthermore, according to Clark, Marquis reagent gives other color reaction with hundreds of drugs. The combination of concentrated sulfuric acid and formaldehyde is a known color reagent (i.e., Le—Rozen test) used for general detection of organic molecules containing aromatic rings (Feigel, F., Spot Tests in Organic Analysis, p. 137, 1966).

Due to low specificity of this reagent, one knows it is negative for Ecstasy wherein it does not turn to a purple/black or blue-black or black color by applying the color reaction.

It is thus apparent that aforementioned single color-producing reagent cannot serve usefully as a field-testing kit for the detection of drugs containing methylenedioxyphenyl group in field conditions, because of the possibility of giving false positive color reactions with so many other substances.

Therefore, when a possible positive color reaction is obtained by the Marquis test, user is advised to proceed to a color test for secondary amine (such as Simon Reagent) for possible presence of Ecstasy, which comprises a secondary amine group. It is thus apparent that a better and more specific reagent should be a color reaction based on the specific reaction of methylenedioxyphenyl group. An early study (M. Beroza, Identification of 3,4-Methylenedioxyphenyl Synergists by Thin-Layer Chromatography, Agriculture and Food Chemistry, Vol. 11, No. 1, p. 51, 1963) indicates that compounds comprising said methylenedioxyphenyl group could be detected by the color developed following reaction with sulfuric acid and chromotropic acid, although MDMA and related drugs were not examined at that study. The color reagent, according to Beroza, is composed of 60% sulfuiric acid and 40% water containing chromotropic acid. The color reagent is used for detection of synergists of insecticides by thin layer chromatography (TLC). However, aforementioned TLC apparatus is heated for 30 min at 105° C. This reagent thus cannot be applied to field-testing of drugs.

A recent method for color reaction of methylendioxyphenyl compounds based on sulfuric acid—chromotropic acid was described by Hideyuki Yamada et al. (Highly Specific and Convenient Color Reaction for Methylenedioxymethamphetamine and Related Drugs Using Chromotropic Acid. Application as a Drug Screening Test, Journal of Health Science, 45(6), pp. 303-308, 1999). In this article the authors described a process for the detection of MDMA and related compounds. The authors stated, "MDMAs did not exhibit any color on adding sulfuric acid . . . namely, if the sample produces a color on adding sulfuric acid alone, it is not an MDMA" (p. 308). The authors also appended a list of drugs that give a color reaction with sulfuric acid—chromotropic acid reagent.

The deficiencies of these tests have led the inventor to develop a chromotropic acid free reagent, specific for phenethylamine derivatives (i.e., amphetamines) drugs, comprising methylenedioxyphenyl group, wherein said reagent having the means to screen out false positive results. This specific reagent allows surprisingly an error-free positive detection of said methylendioxyphenyl amphetamine compounds.

SUMMARY OF THE INVENTION

It is thus an object for the present invention to provide a process for the detection of phenethylamine derivatives, also referred hereby as amphetamine drugs, comprising at least one methylenedioxyphenyl group, comprising, (a) sampling sufficient amount of a material, suspected to comprise of said methylenedioxyphenyl group, comprising (b) admixing said sample with a sufficient amount of a strong acid reagent; (c) observing said sample, and (d) determining a sequence of events, wherein each said event comprises a gradual color appearance at a predetermined time scale.

In one preferred embodiment of the present invention the process as defined above is provided, wherein said process additionally comprising, admixing of a Simon reagent to said sample, so a characteristic blue color reaction is provided in the presence of secondary amines.

In another preferred embodiment of the present invention the process is provided as defined above, wherein said secondary amines are selected from MDMA and MDEA.

In another preferred embodiment of the present invention the process is provided as defined above, wherein said process additionally comprising a step of determining the sample by means of comparing said evaluated sequence of events with a color vs time chart.

In another preferred embodiment of the present invention the process is provided as defined above, wherein said detection is either quantitative or non-quantitative measurement.

In another preferred embodiment of the present invention the process is provided as defined above, wherein said strong acid reagent comprises sulfuric acid or solutions of said acid.

In another preferred embodiment of the present invention the process is provided as defined above, wherein said strong acid reagent is diluted in solvents, miscible with sulfuric acid, selected from at least one of phosphoric acid, hydrochloric acid, methanol and water.

In another preferred embodiment of the present invention the process is provided as defined above, wherein a total volume of said strong acid reagent admixed with said sample is in the range between 0.05 to 5 milliliter.

In another preferred embodiment of the present invention the process is provided as defined above, wherein said strong acid reagent is a solution of said strong acid in a proper diluent, and wherein said acid to said diluent volume ratio ranges between 90:10 to 60:40.

In another preferred embodiment of the present invention, said process is performed in the temperature range of 4° C. to 60° C. and preferably at ambient temperature In another preferred embodiment of the present invention, the process is provided as defined above, for the detection of a trace amount of said phenethylamine derivatives, wherein said amount is preferably in the range of 0.1 to 15 mg.

Further, it is another preferred embodiment to provide the process as defined above, wherein said process is performed in a batch stepwise operation or, at least in part, continuously; and wherein said process is performed either manually or at least in part, automatically. Similarly, said process is preferably provided according to the present invention by means of a machine or any other effective apparatus.

It is another object for the present invention to provide a test kit for the detection of phenethylamine derivatives, also referred hereby as amphetamine drugs, comprising at least one methylenedioxyphenyl group, wherein said test kit comprises a strong acid reagent as defined above.

It is still a preferred embodiment of the present invention the process to provide a testing kit as defined above, wherein said amphetamine drugs to be determined are selected from N-methyl-3,4-methylene-dioxymethamphetamine, 3,4-methylenedioxyamphetamine, 3,4-methylene-dioxyethylamphetamine, and 3-methoxy-4,5-methylene-dioxyamphetamine, N-methyl-1-(3,4-methylene-dioxyphenyl)-2-butaneamine, or 3,4-methylenedioxyphenyl-2-(N-ethyl) butaneamine.

Lastly, it is another preferred embodiment of the present invention to provide a testing kit as defined above, comprising: (a) a strong acid reagent; (b) a color vs time chart comprising means for the detection of a specific drug by means of color and time of appearance; and (c) means for admixing sufficient amount of said strong acid reagent and the suspected materials to give a characteristic color reaction.

DETAILED DESCRIPTION OF THE INVENTION

Contrary to the prior art approached for the color reaction of methylenedioxyphenyl amphetamine type compounds, it has been found that on adding a strong acid as a single component, methylenedioxyphenyl amphetamine type compounds, hereto referred in the present invention as 'amphetamine', developed red-violet colors. Furthermore, it was discovered that the color reaction is acid strength dependent. Thus, the acid strength determines (i) the appearance of the color reaction, wherein in case of acid of sufficient strength, (ii) the time of the appearance of said color reaction. The interval of the color appearance is between instantaneously and several minutes.

According to the mechanism suggested by Yamada et al. (*Journal of Health Science*, 45(6), pp. 303-308, 1999) formaldehyde is released from methylenedioxyphenyl, and the free formaldehyde subsequently reacts with chromotropic acid. However, according to the present invention, red-violet color reaction is developed without chromotropic acid.

According to the present invention it is suggested that at least two reactions occur in said color-formation mechanism. The first reaction is a cleavage of the methylenedioxy group, namely cleavage of one C—O bond (without a release of formaldehyde, as hereto referred by Yamada et al.). The product from the first reaction can subsequently react with other methylenedioxy species, cleaved or not cleaved, to form the violet color. Moreover, amphetamines give an orange color reaction in the presence of sulfuric acid and formaldehyde. The red-violet color obtained, underlines therefore that the color reaction mechanism does not include significant formaldehyde involvement.

Moreover, strong acids, such as sulfuric acid are not considered as a color reagent at all (Feigel F., Spot Tests in Organic Analysis, 1966; Jungreis E., Spot Test Analysis, Clinical, Environmental, Forensic and Geochemical Applications, 1984; Clark, Isolation and Identification of Drugs, 1986). Thus, the probability to get a color reaction by reacting acid with drugs is considerably low.

An aspect of the present invention relates to unique characterization of the hereby-invented reagent to act as a 'clock-color reaction', which is defined according to the present invention, as a color reaction wherein the determined appearance time depends on the acid strength. The higher the strength of acid reagent, shorter is the time for the color to develop. While some drugs give color reaction with acid instantaneously in any concentration, the appearance of the color reaction with amphetamines comprises of methylenedioxyphenyl group is time dependent according to the acid strength. According to the present invention, said chemical clock reaction refers to room temperature yet it is clear that by increasing the temperature, the color develops faster.

Exothermic admixing of water with sulfuric acid (70:30 v/v) is followed with increased temperature. Said strong acid reagent of elevated temperature provided an immediate color reaction when admixed with MDMA, wherein said reagent at room temperature provided said color reaction after a period of about 2 minutes.

The present invention provides an innovative specific reagent to hereto referred amphetamine drugs, wherein said reagent is highly sensitive to even trace amounts of methylenedioxyphenyl amphetamine compounds.

According to the present invention, drugs of methylenedioxy amphetamine family and derivatives are selected from N-methyl-3,4-methylene-dioxymethamphetamine; 3,4-methylenedioxyamphetamine; 3,4-methylene-dioxyethylamphetamine; 3-methoxy-4,5-methylene-dioxyamphetamine; N-methyl-1-(3,4-methylenedioxyphenyl)-2-butaneamine; or 3,4-methylenedioxyphenyl-2-(N-ethyl)butaneamine. It is appreciated that one skilled in the art may use derivatives of said family and thus aforementioned substances are brought as examples for the wider family.

Said strong acid reagent is preferably selected from (i) sulfuric acid and (ii) solutions of said acid with phosphoric acid, hydrochloric acid, methanol and water. The reagent does not react with every methylenedioxyphenyl compound. No color reaction is shown with Narcotine, although it is a methylenedioxyphenyl compound.

According to a preferred embodiment of the present invention, a method for the detection of compounds comprising methylenedioxyphenyl is provided by means of determining a sequence of color changes at a predetermined time course. Said 'detection' is either by examining the presence of said amphethamine drugs, its concentration and/or their specific amount. Thus, for the reason of easiness, the term 'presence' shall refer at the present invention for both quantitative and non-quantitative measurements.

In a preferred embodiment of the present invention, the time scale for determination of aforementioned drugs is in the course of 3 seconds to about 15 minutes. It is appreciated that the period of time required to detect said drugs is affected by various parameters, including yet not restricted to the temperature, the amount of the active group of said drug, the amount of said strong acid reagent, the presence of specific components, inhibitors etc.

Aforementioned process defined above is preferably performed in a batch stepwise operation or, at least in part, continuously. Said process is provided effective either manually or at least in part, automatically. Similarly, said process is preferably provided according to the present invention by means of a machine or any other effective apparatus. Thus, a computer based operation is acknowledged, preferably wherein a personal computer or any other suitable hand held computer provides for the steps selected from batching and sampling the tested material; admixing said strong acid reagent and/or Simon reagent; analyzing said sequence of color changes and determining either quantitatively or non-quantitatively and further on-line or off-line said drug presence in said tested sample.

Preferably, said machine, which in the present invention refers to any effective means to perform at least part of said process automatically, may be in communication with a control box, which may is, for example, said computer. Preferably, the communication is wireless. Alternatively, a cable providing said on-line communication may be used. The operator of said process may enter commands via a keyboard or any suitable command-panel for controlling said process. Said control box may include a display window and software such as Microsoft PowerPoint® for viewing and approving said command prior to its execution by said machine; and for viewing, storing and processing obtained measurement results.

In one preferred embodiment of the present invention, the test kit consists of a sampler, up to three crushable, hermetically sealed glass ampoules and a reaction chamber. The ampoules are filled with the chemicals required to perform the test and includes at least on strong acid reagent. The sampler takes the exact amount of substance needed for test. Suspected material is directly located in the reaction chamber, and the color reaction appears on the sampler.

In another preferred embodiment of the present invention, Simon reagent is used for the detection of secondary amines. Said reagent preferably comprises saturated sodium nitroprusside dihydrate solution in methanol. Said Simon reagent is a sensitive and vulnerable material under certain conditions, so about one drop of said reagent is dropped on said reaction chamber. After few minutes the methanol evaporated and the reagent is dry. Additionally, the test kit comprising two ampoules: ($1^{st}$) sodium carbonate (2%) in water and ($2^{nd}$) acetaldehyde (10%) in ethanol.

In another preferred embodiment of the present invention is a method to use aforementioned Simon reagent containing test kit, comprising (1) sampling suspected material with said sampler so said suspected material to be tested is inserted to the reaction chamber containing sodium nitroprusside in dry form-; (2)/breaking $1^{st}$ ampoule and gently shaking its content into said reaction chamber; (3)/breaking $2^{nd}$ ampoule and inserting its content to said reaction chamber. Characteristic blue color approves presence of secondary amine.

In another preferred embodiment, a water solution (2% v/v) of said sodium nitroprusside is prepared. Nevertheless, said solution is sensitive to light and characterized with acknowledged short self-life.

While the invention will now be described in connection with certain preferred embodiments in the following examples so that aspects thereof may be more fully understood and appreciated, it is not intended to limit the invention to these particular embodiments. On the contrary, it is intended to cover all the alternatives, modifications and equivalent as may be included within the scope of the invention as defined by the appended claims. Thus, the following examples, which include preferred embodiments, will serve to illustrate the practice of this invention, it being understood that the particulars shown are by way of example and for purpose of illustrative discussion of preferred embodiments of the present invention only and are presented in the cause of providing what is believed to be the most useful and readily understood description of formulation procedures as well as of the principles and conceptual aspects of the invention.

EXAMPLES

The following description is provided to enable any person skilled in the art to make and use the invention, and sets forth the best modes contemplated by the inventor of carrying out this invention. Various modifications, however, will remain apparent to those skilled in the art, since the generic principles of the present invention have been defined specifically to provide for the detection of hereto referred amphetamines and a testing kit for the same.

Example 1

Color Reaction of a Strong Acid Reagent with Various Materials

A trace amount (e.g., 1-3 milligrams) of drugs are added to a small test tube. 0.5 ml of 98% sulfuric acid is added to said test tube. The color development was examined visually and described below:

Positives: MDA, MDMA, MDEA, MBDB, MDP-2-EB—immediate appearance of red-violet color.
Other colors: Thebaine—immediate appearance of red-orange; Diphenhydramine, Furosemide, Naproxen—yellow; Prometazine—pink and Nicotineamide, Clomiphene citrate—brown.
Negative (no color): Amphetamines, such as Amphetamine, Methamphetamine, Nexus, DOB, Ephedrine; other pharmaceuticals and illicit drugs, comprising Metadone, Cocaine, Heroin, Paracetamol, Procaine, Phenthylene, Codeine, Caffeine, Papaverine, Pentobarbital, Nitrazepam, Diazepam, Flunitrazepam, Oxazepam, Morphine, Efedrine, Methaqualone, Lignocaine, Tetracaine, Phenacetin, Phenmetrazine, Meprobamate, Antipyrine, Chinin, Pethidine, Strychnine, Barbital, Cyclobarbital, Amobarbital, Propoxyphen, Atropine, Homatropine, Phencyclidine (PCP), Scopolamine, Narcotine, Chloropromazine, Perphenazine, Fluconazole, hydroxyine, pseudoephedrine, Doxazosim, Sulphamethoxazole, Tolbutamide, Propylthiouracil, Cephalexin, Loperamide, Chlorothiazide, Felodipine, Quinidine bisulphate, Finasteride, Benzocaine, Oxprnolol, Alendromate, Bromocripitine, Ranitidine, Fluoxentine, Enalapril maleate, Propoxyphene, Famotidine, Tranexamic acid, Amoxycillin, Cloxacillin, Candesatan cilexetil, Cimetidine, Bromazapam, Haloperidol, Bromahexine, statin compounds such as Simvstatine, Valporic acid, levodopa and Norfloxacin.

It should be mentioned that Chloropromazine and Perphenazine that gave pink color with sulfuric acid and chromotropic acid (as previously described by Yamada et al.)—do not give any color reaction in the presence of sulfuric acid as a single component.

Example 2

Clock Reaction with Queous Solutions of Sulfuric Acid

As described previously the color reaction is not developed immediately, but begins with a pale violet color, which gradually intensified. The time in the table indicates the appearance time of a faint color.

A trace amount (i.e., 3 milligrams) of drugs were added to a small test tube. 0.5 ml of different aqueous sulfuric acid compositions was added to the test tube. The color development was examined visually:

| | Time of Color Appearance (sec) | | | | | | | |
|---|---|---|---|---|---|---|---|---|
| $H_2SO_4/H_2O$ (v/v) | MDMA | MDA | MDEA | MBDB | MDP-2-RB | Thebaine | Diphenhydramine | Prometzine |
| 90/10 | 5 | 5 | 5 | 5 | 0 | 0 | 0 | 0 |
| 80/20 | 20 | 20 | 20 | 20 | 20 | 0 | 0 | 0 |
| 75/25 | 60 | 60 | 60 | 60 | 60 | 0 | 0 | 0 |
| 70/30 | 120 | 120 | 120 | 120 | 120 | 0 | 0 | 0 |
| 60/40 | ND* | ND* | ND* | ND* | ND* | 0 | 0 | 0 |

ND* - No color reaction was detected after 15 minutes.

It should be mentioned that Clomiphene citrate, Furosemide, Naproxen and Nicotineamide, that give color reaction with 98% sulfuric acid, do not give color reaction with 75% sulfuric acid aqueous solution.

Example 3

Clock Reaction with Sulfuric Acid/HCl (32%)

The reactions were performed as described above, and color development was examined visually:

| | Time of Color Appearance (sec) | | | | | | | |
|---|---|---|---|---|---|---|---|---|
| $H_2SO_4/HCl$ (v/v) | MDMA | MDA | MDEA | MBDB | MDP-2-RB | Thebaine | Diphenhydramine | Prometzine |
| 80/20 | 0 | 0 | 0 | 0 | 0 | 0 | 0 | 0 |
| 70/30 | 60 | 60 | 60 | 60 | 60 | 0 | 0 | 0 |
| 60/40 | ND* | ND* | ND* | ND* | ND* | 0 | 0 | 0 |

ND* - No color reaction was detected after 15 minutes.

Example 4

Clock Reaction with Sulfuric Acid/Methanol

The reactions were performed as described above, and color development was examined visually:

|  | Time of Color Appearance (sec) | | | | | | | |
|---|---|---|---|---|---|---|---|---|
| $H_2SO_4/$ $CH_3OH$ (v/v) | MDMA | MDA | MDEA | MBDA | MDP-2-RB | Thebaine | Diphenhydramine | Prometzine |
| 90/10 | 5 | 5 | 5 | 5 | 5 | 0 | 0 | 0 |
| 80/20 | 10 | 10 | 10 | 10 | 10 | 0 | 0 | 0 |
| 70/30 | 60 | 60 | 60 | 60 | 60 | 0 | 0 | 0 |

Example 5

Clock Reaction with Sulfuric Acid/Phosphoric Acid (85% aqueous solution)

The reactions were performed as described above, and color development was examined visually:

|  | Time of Color Appearance (sec) | | | | | | | |
|---|---|---|---|---|---|---|---|---|
| $H_2SO_4/$ $H_3PO_4$ (v/v) | MDMA | MDA | MDEA | MBDA | MDP-2-RB | Thebaine | Diphenhydramine | Prometzine |
| 80/20 | 10 | 10 | 10 | 10 | 10 | 0 | 0 | 0 |
| 70/30 | 20 | 20 | 20 | 20 | 20 | 0 | 0 | 0 |
| 60/40 | 105 | 105 | 105 | 105 | 105 | 0 | 0 | 0 |

It is evident to those who are skilled in the art that the preset invention is not limited to the details of the forgoing illustrative examples, and that the present invention may be embodied in other specific forms without departing from the essential attributes thereof, and it is therefore desired that the present embodiments and examples be considered in all respects as illustrative and not restrictive, reference being made to the appended claims, rather than to the foregoing description, and all changes which come within the meaning and range of equivalency of the claims are therefore intended to be embraced therein.

The invention claimed is:

1. A process for the detection of drugs of methylenedioxy amphetamine family and derivatives, consisting essentially of:
   a) sampling sufficient amount of a material, suspected to contain a methylenedioxyphenyl group;
   b) admixing said sample with a sufficient amount of a strong acid reagent selected from the group consisting of sulfuric acid or mixtures of (i) sulfuric acid and (ii) a diluent selected from phosphoric acid, hydrochloric acid, water or methanol wherein said mixtures consist of (i) and (ii) in a 90:10 to 60:40 volumetric ratio;
   c) detecting a gradual appearance of color over a predetermined amount of time depending on the strength of said strong acid reagent and determining accordingly the presence of said methylenedioxy amphetamine drugs.

2. The process according to claim 1, wherein said detected color is red-violet.

3. The process according to claim 1, wherein said detection is either a quantitative or a non quantitative measurement.

4. The process according to claim 1, wherein a total volume of said strong acid reagent admixed with the sample is in the range of 0.05 to 5 ml.

5. The process according to claim 1, wherein said strong acid reagent is in a concentration of 50% to 100% (v/v).

6. The process according to claim 1, wherein said strong acid reagent is in a concentration range of 70% to 80% (v/v).

7. The process according to claim 1, wherein said process is conducted at a temperature of from 40° C. to 60° C.

8. The process according to claim 1, wherein said process is conducted at a temperature of from 10° C. to 27° C.

9. The process according to claim 1, performed with a trace amount of said phenethylamine derivatives, wherein said amount is in the range of 0.1 to 15 mg.

10. The process according to claim 1, performed manually.

11. The process according to claim 1, performed at least in its part automatically.

12. The process according to claim 1, performed by a batch stepwise operation.

13. The process according to claim 1, performed at least in its part continuously.

14. A process for the detection of methylenedioxy amphetamine family and derivatives consisting essentially of:
   a) sampling a sufficient amount of a material suspected to contain a methylenedioxyphenyl group;
   b) admixing said sample with a sufficient amount of a strong acid selected from the group consisting of sulfuric acid or mixtures of (i) sulfuric acid and (ii) a diluent selected from phosphoric acid, hydrochloric acid, water or methanol wherein said mixtures consist of (i) and (ii) in a 90:10 to 60:40 volumetric ratio;
   c) detecting a gradual appearance of color over a predetermined amount of time depending upon the strength of said strong acid reagent, and determining the presence of said methylenedioxy amphetamine drugs; and
   d) if the presence of a methylenedioxy amphetamine drug is determined, additionally consisting essentially of admixing a Simon reagent with said sample, whereby a characteristic blue color reaction occurs in the presence of secondary amines to confirm the presence of a secondary amine.

15. The process according to claim 14, wherein said secondary amines are selected from N-methyl-3,4-methylenedioxymethamphetamine and 3,4-methylenedioxyethylamphetamine.

16. A process for the detection of methylenedioxy amphetamine family and derivatives consisting essentially of:
 a) sampling a sufficient amount of a material suspected to contain a methylenedioxyphenyl group;
 b) admixing said sample with a sufficient amount of a strong acid selected from the group consisting of sulfuric acid or mixtures of (i) sulfuric acid and (ii) a diluent selected from phosphoric acid, hydrochloric acid, water or methanol wherein said mixtures consist of (i) and (ii) in a 90:10 to 60:40 volumetric ratio;
 c) detecting a gradual appearance of color over a predetermined amount of time depending upon the strength of said strong acid reagent, and determining the presence of said methylenedioxy amphetamine drugs;
 d) opening a container comprising sodium carbonate (1%) in water and gently shaking its contents into a reaction chamber which comprises a drop of sodium nitroprusside in dry ethanol; and
 e) opening a container comprising acetaldehyde (10%) in ethanol and inserting its contents into said reaction chamber, wherein formation of characteristic blue color denotes the presence of secondary amine.

* * * * *